US012629019B2

(12) United States Patent (10) Patent No.: US 12,629,019 B2
Tripathi et al. (45) Date of Patent: May 19, 2026

(54) OCULAR FEEDBACK SYSTEM AND METHOD

(71) Applicant: NEXUS CLINICAL LLC, Weston, FL (US)

(72) Inventors: Pradeep Ram Tripathi, Miami Beach, FL (US); Robert W. Connors, Lake Barrington, IL (US); Nishant Ram Tripathi, Miami Beach, FL (US); Derek King, Hollywood, FL (US)

(73) Assignee: Nexus Clinical LLC, Weston, FL (US)

( * ) Notice: Subject to any disclaimer, the term of this patent is extended or adjusted under 35 U.S.C. 154(b) by 263 days.

(21) Appl. No.: 18/121,834

(22) Filed: Mar. 15, 2023

(65) Prior Publication Data

US 2023/0293006 A1 Sep. 21, 2023

Related U.S. Application Data

(60) Provisional application No. 63/320,373, filed on Mar. 16, 2022.

(51) Int. Cl.
| | |
|---|---|
| *A61B 3/11* | (2006.01) |
| *A61B 3/14* | (2006.01) |
| *G06V 40/18* | (2022.01) |
| *H04N 23/57* | (2023.01) |

(52) U.S. Cl.
CPC .............. *A61B 3/112* (2013.01); *A61B 3/14* (2013.01); *G06V 40/193* (2022.01); *H04N 23/57* (2023.01)

(58) Field of Classification Search
CPC .. A61B 3/112; A61B 3/14; A61B 5/01; A61B 5/021; A61B 5/02416; A61B 5/0077;

A61B 5/1103; A61B 5/1104; A61B 3/113; A61B 5/163; A61B 5/165; A61B 5/4839; A61B 5/4848; A61B 5/6803; A61B 5/6821; G06V 40/193; H04N 23/57

See application file for complete search history.

(56) References Cited

U.S. PATENT DOCUMENTS

| | | | | |
|---|---|---|---|---|
| 7,682,021 | B2 * | 3/2010 | Sabel | A61B 3/024 |
| | | | | 351/203 |
| 9,301,678 | B2 * | 4/2016 | Hirsh | A61B 5/1128 |
| 10,039,445 | B1 * | 8/2018 | Torch | A61B 5/18 |
| 10,182,755 | B2 * | 1/2019 | Ohayon | G06T 7/0014 |
| 2008/0234322 | A1 * | 9/2008 | Syroid | A61K 31/02 |
| | | | | 514/731 |

(Continued)

*Primary Examiner* — Dmitriy Bolotin
(74) *Attorney, Agent, or Firm* — K&L Gates LLP

(57) ABSTRACT

An ocular feedback system includes a first camera assembly including a first frame worn by a first user and at least one first camera supported by the first frame. The first camera produces a first camera output concerning the first user's eyes. A second camera assembly includes a second frame worn by a second user and at least one second camera supported by the second frame. The second camera produces a second camera output concerning the second user's eyes. At least one computer is configured to build an established outcome determiner based on an analysis of the at least one first and second camera outputs. The computer compares the established outcome determiner to at least one third camera output concerning a third user's eyes taken by at least one third camera supported by a third frame of a third camera assembly worn by the third user.

33 Claims, 4 Drawing Sheets

(56)                    References Cited

U.S. PATENT DOCUMENTS

| | | | |
|---|---|---|---|
| 2011/0077548 A1* | 3/2011 | Torch .................... | A61B 5/165 |
| | | | 600/558 |
| 2014/0268047 A1* | 9/2014 | Hirsh .................... | A61B 3/112 |
| | | | 351/246 |
| 2016/0192838 A1* | 7/2016 | Hirsh .................... | A61B 3/112 |
| | | | 351/246 |
| 2024/0293630 A1* | 9/2024 | Tseng ................... | A61F 7/0085 |

\* cited by examiner

OCULAR FEEDBACK SYSTEM AND METHOD

PRIORITY CLAIM

This application claims priority to and the benefit as a non-provisional application of U.S. Provisional Patent Application No. 63/320,373, filed on Mar. 16, 2022, the entire contents of which are hereby incorporated by reference and relied upon.

BACKGROUND

The present disclosure relates generally to feedback and more specifically to feedback regarding a user's reaction to a drug, medicine, medicament, or other phenomenon.

Today, a doctor's dose of a particular drug is based generally on the severity of an illness and patient conditions such as age, weight, sex, etc. Oftentimes drugs require trial and error to determine the right drug and the right dose. The feedback from such trial and error approach is a sometimes long term determination of whether the drug and dose are correct.

Certain types of drugs, such as those for mental conditions, anxiety and the like may be hard to evaluate regarding effectiveness. Such hardship even further complicates drug choice and drug dose.

A need for an improved way to prescribe a drug and its dose is needed accordingly.

SUMMARY

The examples described herein disclose a system and method that use feedback from a camera to help make a determination as to a user's condition. The system and method in one embodiment mount one or more camera on a frame that is worn by the user in such a way that the one or more camera can record a video image or still image of one or both of the user's eyes. The frame may be part of a pair of glasses, which may or may not actually have lenses, and which may or may not be prescription glasses. The frame may have extensions such that the one or more camera is set away from the user's eyes, e.g., to enhance the video image taken by the camera. The frame may also be attached to a strap configured to be worn about a user's head. The frame in an embodiment is provided with a rechargeable or replaceable battery that powers the one or more camera and any other electronics, such as a display device and possibly a microprocessor and video controller. The frame, the one or more camera, and any associated electronics may be referred to herein as a camera assembly.

The one or more camera of the assembly may, for example, be a five megapixel camera capable of 720p video recording. The display device may, for example, be a 640×360 Himax HX7309 LCoS display. The microprocessor may, for example, be a Texas Instruments OMAP 4430 SoC 1.2 Ghz processor or be an Intel Atom processor. The camera assembly may be provided with, e.g., 16 to 32 gigabytes of storage and 1 gigabyte of RAM. The power supply for the camera assembly may for example be a 780 to 820 mAh battery and may be provided with a fast recharge.

It is contemplated that the system of the present disclosure encompass multiple camera assemblies each outputting to various recipients that may analyze the recorded video image or camera output. For example, the cameras may output to the user's smart device, e.g., smart phone. Alternatively or additionally, the cameras may output to a computer, which may be the user's computer or be the computer of a clinic, service, or other entity interested in analyzing the camera output.

The user's smart device or smartphone in an embodiment may download an application ("app") that analyzes the one or more camera output for a user. The user's smart device or smartphone in an embodiment may access a cloud or other server based software for analyzing the one or more camera output for the user. The user's smart device or smartphone alternatively or additionally relays the one or more camera output to the user's clinic, service, or other interested entity computer, which includes the software for analyzing the one or more camera output for the user. The user's smart device or smartphone alternatively or additionally relays the one or more camera output to the cloud or other server, which includes the software and memory storage for analyzing and storing the one or more camera output for the user, e.g., for artificial intelligence purposes described herein.

As discussed above, the user's clinic, service, or other interested entity computer may include the software for analyzing the one or more camera output for the user. The results of such analysis may be displayed or otherwise communicated at the computer or be sent back to the user's smart device or smart phone for display and/or other form of communication.

The user's clinic, service, or other interested entity computer may alternatively or additionally relay the one or more camera output for the user to the cloud or other server, which includes the software and memory storage for analyzing and storing the one or more camera output for the user, e.g., for artificial intelligence purposes described herein. The results of such analysis may be displayed or otherwise communicated, e.g., visually and/or audibly, at the camera assembly worn by the user, at the user's smart device or smart phone, or at the clinic, service, or other interested entity computer. The camera assembly, as discussed herein, may be provided with a display device, microprocessor, and video controller for analyzing and displaying the output of the analysis directly to the user, e.g., in real time or virtually in real time.

The one or more camera is used in one embodiment to record the reaction to a stimulus given to or applied to the wearer of the camera assembly. Example stimuli include prescription drugs, medicines or medicaments, homeopathic medicines, meditation, exercise, yoga, cannabis (including cannabidiol ("CBD") and other derivatives), a change in environment, and music.

The one or more camera worn by the user may be focused, for analysis, on any one or more ocular or eye related feature or phenomenon, including the user's retina, visual cortex, eye movement (up/down, left/right), blinking, and eyebrow movement. The results of the analysis may be combined with the results from one or more other sensor, such as a blood pressure sensor, a pulse oximeter, a blood sugar sensor, and a user temperature sensor.

The analysis of the output of the one or camera may look to provide an indication of the mental state of the user, including any one or more of the following: physical pain, stress, fear/anxiety, happiness/euphoria, calmness, concentration/focus, anger, and medical anomaly or disorder.

The analysis of the one or more camera output, e.g., for any of the stimuli listed herein, and focusing on any ocular or eye related feature or phenomenon discussed herein, may involve the comparison of the user's camera output results to an established outcome determiner, such as a range of results. Based on the comparison of the user's results to the outcome determiner, the ocular feedback system and method of the present disclosure may form one or more conclusion, diagnosis, and/or recommendation. To establish the outcome determiner, e.g., range of results, it is contemplated to aggregate population data. Here is where the many camera assemblies are used by the present system. Over time, as more data is collected from more and more different camera assemblies, and more results are verified, e.g., via a third party such as outside third party testing and a doctor's diagnosis. The outcome determiner may be further built based on a collective agreement (e.g., 80 percent of people having particular camera result report feeling happiness/euphoria) such that the outcome determiner becomes better established and may be able to predict and provide more and more conclusions, diagnosis, and/or recommendations.

It is contemplated that the collective database be bolstered by additional user input. That is, the collective data is not just data from the camera assemblies, but also data inputted by the user, which may help categorize the data. The user may, for example, provide data concerning other medications taken, known user health conditions, exercise habits, eating and drinking habits, for example, which are relevant to the particular analysis being performed. The user inputted data may be used to form sub-groups, e.g., for a Glaucoma analysis, the user's data may be compared to the whole population and/or to subgroups of users having the same conditions such as age range, ethnicity, etc. The ocular feedback system of the present disclosure becomes more confident in its conclusions and is able to make more and more conclusions as the data set, including camera assembly data and user input data increases. Trending analysis may be possible based on a change in the conditions of patients with certain ailments and treatments.

The analysis may be performed in real time and provide discrete tracking of the user, which facilitates comparison of the user's data to the outcome determiner developed from the population data, including any relevant subgroups. The outcome determiner may also be based on historical data for a particular user, e.g., a trend based on the individual indicates that a certain user event is likely to happen. So the outcome determiner does not have to be based on data from other users and may alternatively or additionally be based on historical user data. Comparison of the user data with the population data may discover a patient condition that is not the focus of the present analysis, e.g., unknown conditions based on data comparison similarities with subgroups of the population diagnosed with such conditions.

A goal of the collective population and individual data of the present system is to provide a more accurate measure of the dosing of a medication, the effectiveness of treatment, and the selection of the best type of treatment.

In an embodiment, the camera assembly of the ocular feedback system of the present disclosure includes only one or more inwardly looking camera that is able to record a desired aspect of the user's eye or eyes. In an alternative embodiment, the camera assembly is additionally provided with one or more outwardly looking camera that records the user's environment, such as a workplace environment, social environment, entertainment environment, relaxation environment, and the like. The software of the system is configured in one embodiment to build correlations between user emotional states (inward looking camera results) and environmental factors (outward looking camera results). The correlations may for example include an outward looking camera output cause and an inward looking camera output effect. The software of ocular system may be further configured to build a historical database for the user, which may be used predict reactions for new encounters based on recorded correlations for the user in past encounters.

The ocular system may in certain embodiments use only the outwardly looking camera results. For example, in a workplace environment, it may be more useful to evaluate what the user is looking at than what the user may be feeling in terms of whether the user is paying attention to work or to some distraction or non-work activity. When the user is paying attention to work, however, it may be useful to monitor the inward looking one or more camera to evaluate the user's mental state while being focused on the user's work.

In light of the disclosure herein and without limiting the disclosure in any way, in multiple aspects of the present disclosure, any of the features, structures and functionality presented in any of AI driven and environmental claims 1 to 21 may be combined with any other features, structures and functionality presented in any of AI driven and environmental claims 1 to 21, which in turn may be combined with any other features, structures and functionality presented in any one or more of camera driven claims 1 to 15.

In another aspect of the present disclosure, any of the structure and functionality disclosed in connection with FIGS. 1 to 4 may be included or combined with any of the other structure and functionality disclosed in connection with FIGS. 1 to 4.

In light of the present disclosure and the above aspects, it is an advantage of the present disclosure to provide an improved way to evaluate the effectiveness of a medical treatment for a user of the present ocular feedback system of the present disclosure.

It is another advantage of the present disclosure to provide an improved way to dose drugs, medicines and medicaments taken by a user of the present ocular feedback system of the present disclosure.

It is a further advantage of the present disclosure to provide an improved way to perform medical diagnostics for a user of the present ocular feedback system of the present disclosure.

It is still another advantage of the present disclosure to provide an improved way to perform workplace efficiency measurements for a user of the present ocular feedback system of the present disclosure.

It is still a further advantage of the present disclosure to provide an improved way to correlate real world environmental effects with the mental state of a user of the present ocular feedback system of the present disclosure.

It is yet another advantage of the present disclosure to provide an improved way to determine the effects of visual and audio stimulation on the mental state of a user of the present ocular feedback system of the present disclosure.

It is yet a further advantage of the present disclosure to provide an ocular feedback system that uses population databases and artificial intelligence to build standards, categories, flags and other ways to evaluate the inwardly looking and/or outwardly looking camera outputs of the system.

Moreover, it is an advantage of the present disclosure to provide an ocular feedback system that builds historical databases and predictive trends for individual user's to evaluate the camera outputs of the system and to predict user conditions, such as medical ailments, reaction to treatment, and emotional responses to environmental stimuli.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
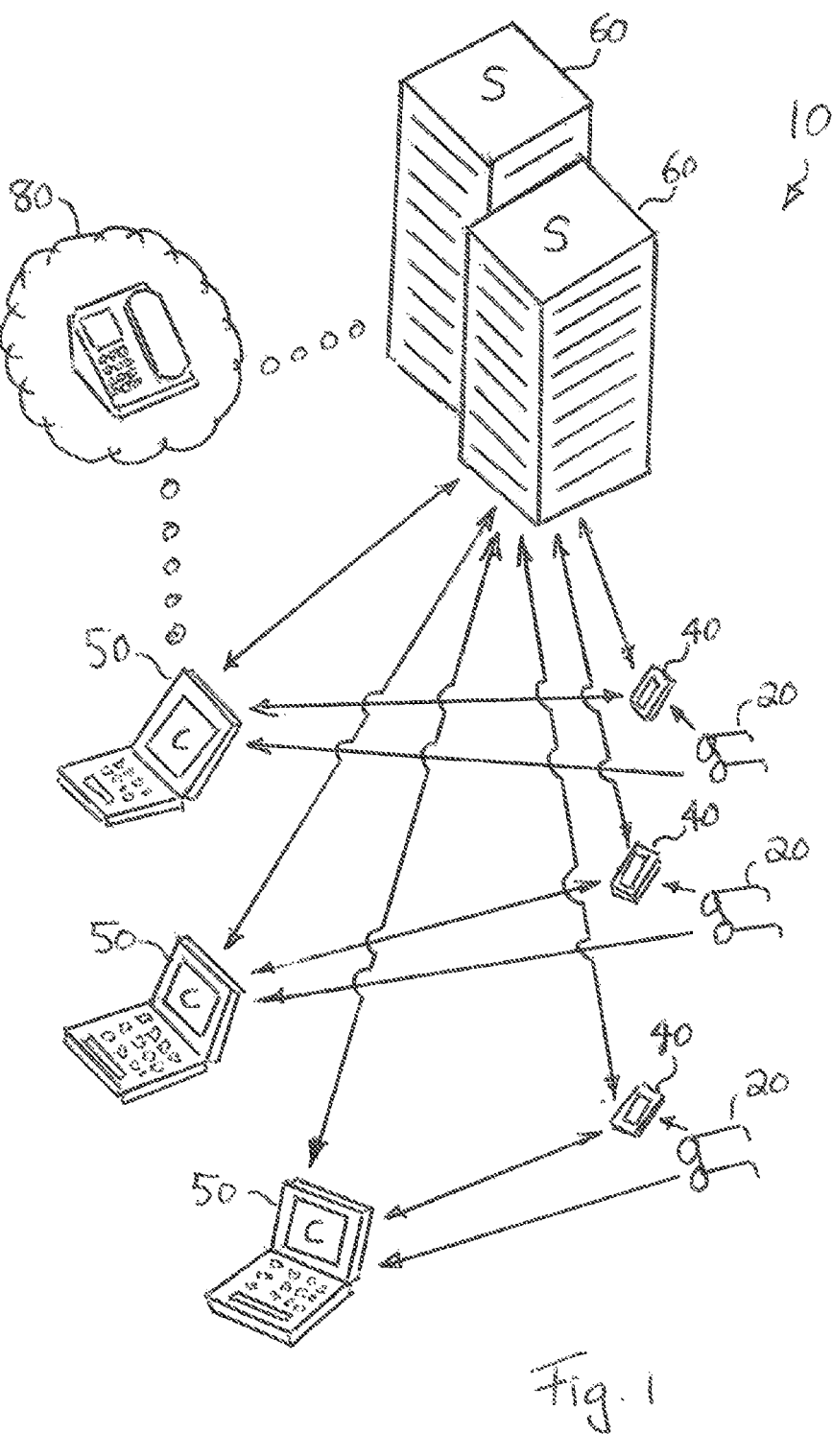
FIG. 1 is a schematic perspective view of one embodiment of the ocular feedback system of the present disclosure.
Figure 2:
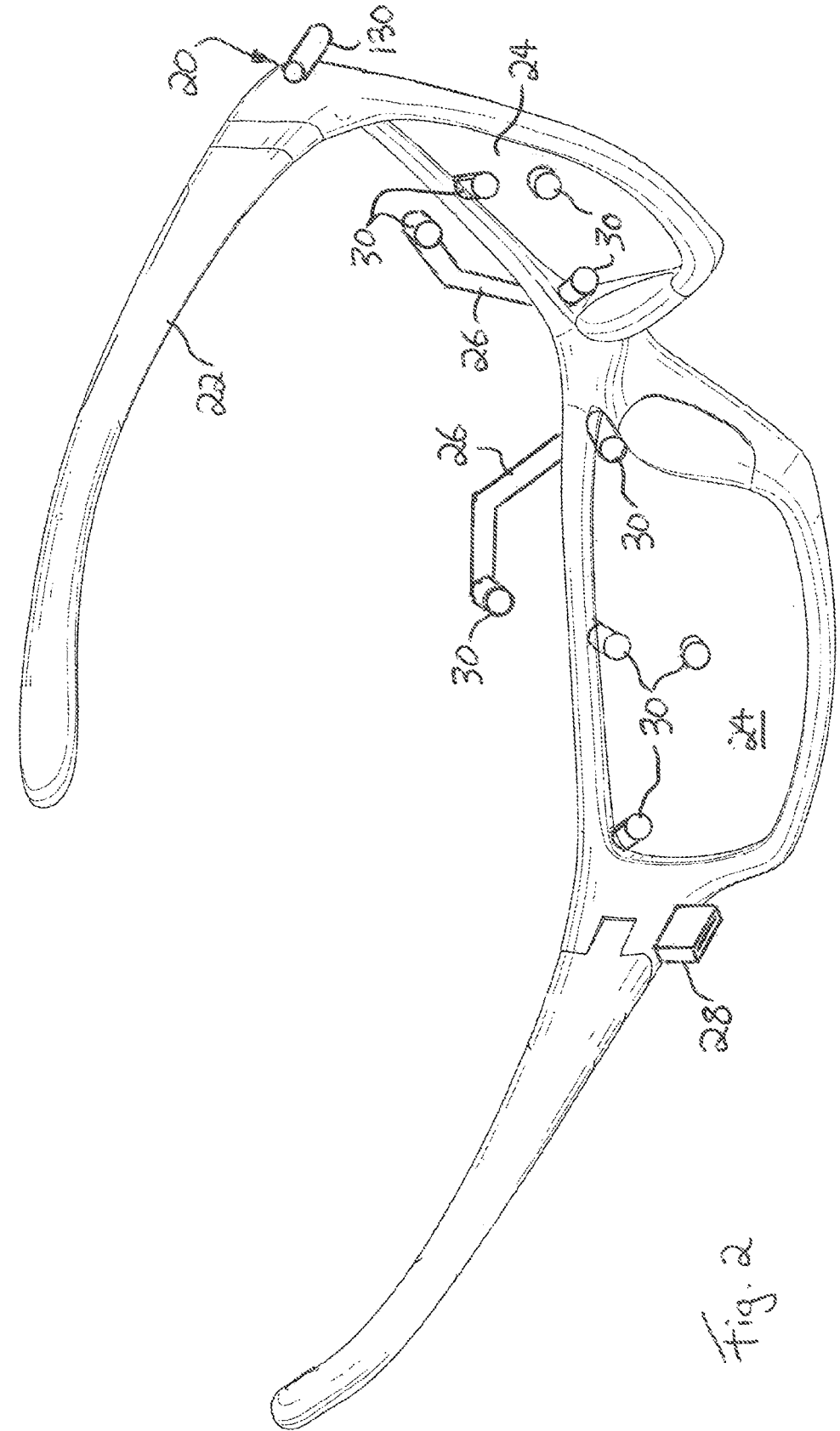
FIGS. 2 to 4 are bottom perspective, rear, and side views, respectively, of one embodiment for a camera assembly for use with the ocular feedback system of the present disclosure.
Figure 3:
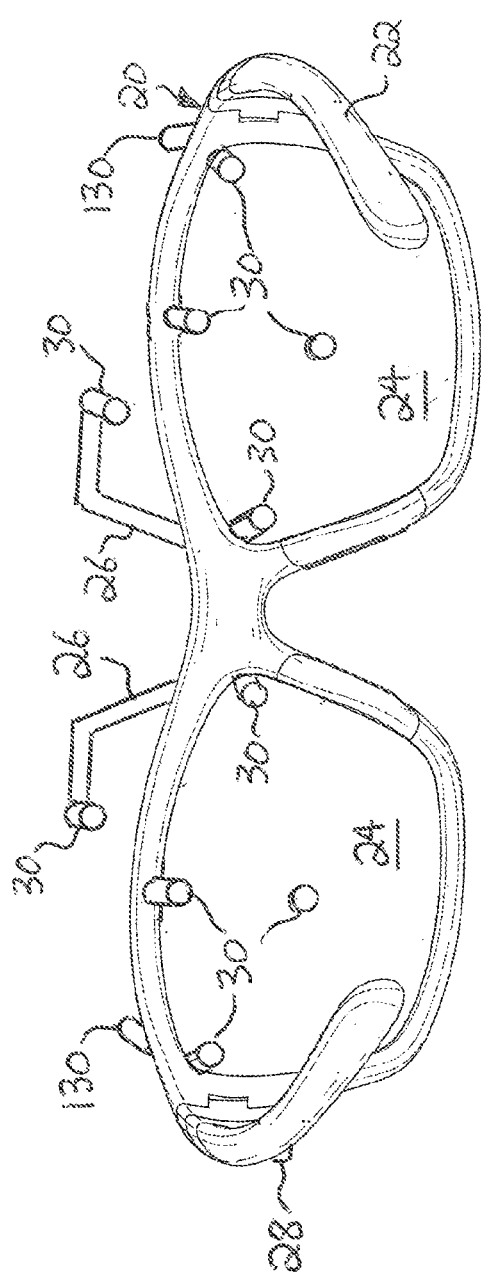
Figure 4:
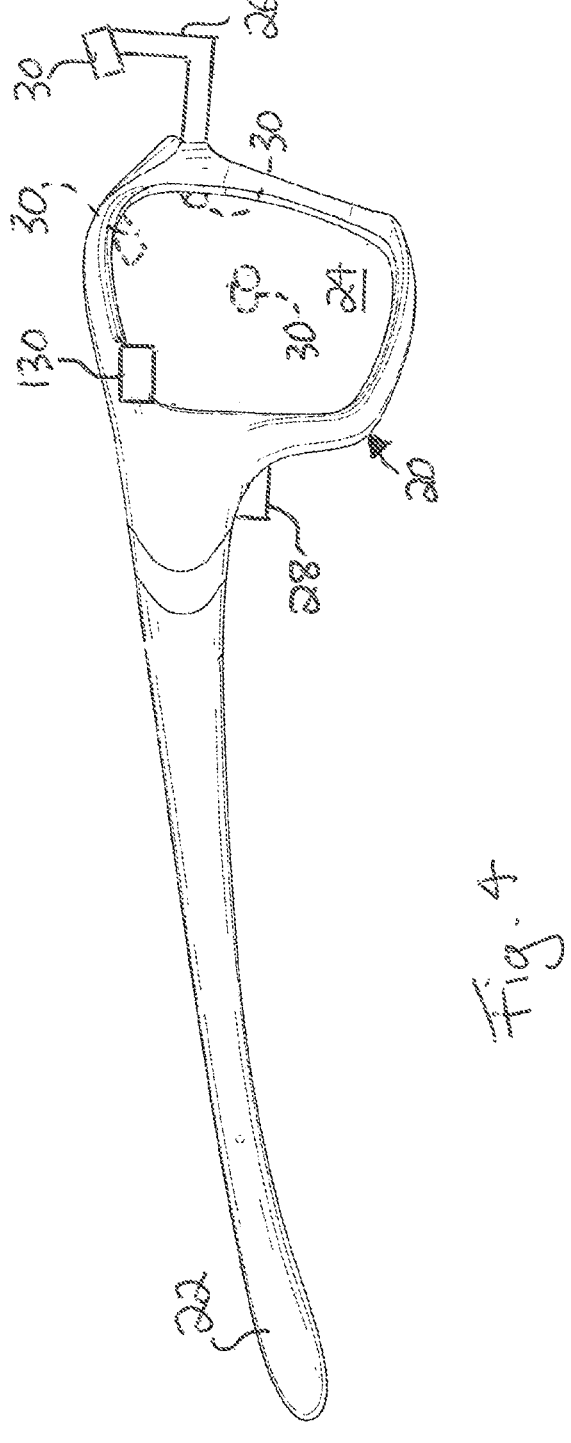

Referring now to the drawings and in particular to FIGS. 1 to 4, an embodiment for an ocular feedback system of the present disclosure is illustrated by system 10. System 10 employs methodology that uses feedback from a camera assembly 20 to help make a determination as to the user's condition. FIGS. 2 to 4 illustrate that ocular feedback system 10 in one embodiment mounts one or more inward looking camera 30 on a frame 22 that is worn be the user in such a way that one or more camera 30 can record a video image or camera output of one or both of the user's eyes. Frame 22 may be plastic or metal and be part of a pair of glasses, which may or may not actually have glass or transparent plastic 24, and which may or may not be prescription glasses. Frame 22 may also be attached to a strap (not illustrated) configured to be worn about a user's head. Frame 22 may have extensions 26 on which camera 30 is mounted, such that one or more inward looking camera 30 is set away from the user's eyes, e.g., to enhance the video image taken by the camera. Frame 22, in an embodiment, is provided with a power supply, such as a rechargeable or replaceable battery 28 that powers one or more camera 30 and any other electronics supported by frame 22, such as a display device, video controller, and possibly a microprocessor (not illustrated).

In an embodiment, camera assembly 20 of ocular feedback system 10 of the present disclosure includes only one or more inwardly looking camera 30 that is able to record, for many uses discussed herein, a desired aspect of the user's eye or eyes. In an alternative embodiment, camera assembly 20 is additionally provided with one or more outwardly looking camera 130 that records the user's environment, such as a workplace environment, social environment, entertainment environment, relaxation environment, and the like. The software of ocular feedback system 10 is configured in one embodiment to build correlations between user emotional states (inward looking camera results) and environmental factors (outward looking camera results). The software of ocular feedback system 10 may be further configured to build a historical database for the user, which may be used predict reactions for new encounters based on recorded correlations for the user in past encounters.

Ocular feedback system 10 may in certain embodiments use only results from the one or more outwardly looking camera 130. For example, in a workplace environment, it may be more useful to evaluate what the user is looking at than what the user may be feeling in terms of whether the user is paying attention to work or to some distraction or non-work activity. When the user is paying attention to work, however, it may be useful to monitor the inward looking one or more camera 30 to evaluate the user's mental state while being focused on the user's work.

FIGS. 3 and 4 accordingly illustrate that frame 22 in certain embodiments may further support one or more outwardly looking camera 130 that records and captures the user's environment, e.g., while one or more inward looking camera 30 records the user's reaction to same. Frame 22, one or more in ward looking camera 30, optional one or more outwardly looking camera 130, and any associated electronics are referred to herein as a camera assembly 20.

One or more inward and outward looking camera 30, 130 of assembly 20 may for example be a five megapixel camera capable of 720p video recording. A display device if provided by assembly 20 may for example be a 640×360 Himax HX7309 LCoS display. A microprocessor if provided by assembly 20 may for example be a Texas Instruments OMAP 4430 SoC 1.2 Ghz processor or be an Intel Atom processor. Camera assembly 20 may further be provided with, e.g., 16 to 32 gigabytes of storage and 1 gigabyte of RAM. Power supply 28 for camera assembly 20 may for example be a 780 to 820 mAh battery and may be provided with a fast recharge.

It is contemplated to sputter, photoetch, or otherwise deposit electrically conductive traces (not illustrated), such as copper traces, that run from power supply 28 to one or more inward and outward looking camera 30, 130 and any other electronics if provided to power same. The conductive traces if provided on the surface of frame 22 are in one embodiment covered by a protective tape or film (not illustrated). The conductive e.g., copper, traces may alternatively or additionally be located on the inner surface of a component of frame 22 that is mated with another component of frame 22 during manufacturing to cover and hide the copper traces, which are then extend through one of the frame components to reach cameras 30, 130 and any other electronics of camera assembly 20. Thin, electrically conductive wires, e.g., copper wires, may alternatively or additionally be run within components of frame 22 from power supply 28 to cameras 30, 130 and any other electronics of camera assembly 20.

FIGS. 2 to 4 illustrate example locations for inward and outward looking cameras 30, 130. Inward looking cameras 30 may be provided for example anywhere, and in any number, along the portion of frame 22 surrounding glass or transparent plastic 24 (or around a hole if glass/plastic 24 is not provided). Frame-mounted inward looking cameras 30 in the illustrated embodiment are mounted at an angle so as to be oriented towards and focusable on a desired portion of the user's one or more eye, e.g., the retinas. One or more inward looking camera 30 may alternatively or additionally be secured, e.g., adhered, to one or both of glass/plastic lenses 24 held within frame 22. Camera 30 located on glass/plastic 24 may operate wirelessly or via one or more conductive lead extending from power source 28. Cameras 30 located on glass/plastic lenses 24 are very small in an embodiment so as not to appreciably impact the user's vision. FIGS. 2 to 4 illustrate that extensions 26 may extend in three (or less) dimensions from frame 22 over desired distances, and that inward looking cameras 30 may be oriented with respect to extensions 26 so as to provide an optimized camera distance and orientation for video recording one or both of the user's eye, including a desired portion thereof. Extensions 26 may be molded with or attached to frame 22.

FIG. 1 illustrates that it is contemplated for ocular feedback system 10 of the present disclosure to encompass multiple camera assemblies 20, each outputting to various recipients that may analyze the recorded video image or camera output. For example, inward and outward looking cameras 30, 130 may output to the user's smart device 40, e.g., smart phone. Alternatively or additionally, cameras 30, 130 may output to a computer 50, which may the user's computer or be the computer or a clinic, service or other entity interested in analyzing the camera output.

The user's smart device or smartphone 40 in an embodiment may download an application ("app") that analyzes the output of one or more camera 30, 130 for a user. The user's smart device or smartphone 40 in an embodiment may access software stored at cloud or other computer server 60 for analyzing the output of one or more camera 30, 130 for the user. The user's smart device or smartphone 40 alternatively or additionally relays the output of one or more camera 30, 130 to the user's clinic, doctor's office, service or other interested entity computer 50, which includes the software for analyzing the output of one or more camera 30, 130 for the user. The user's smart device or smartphone 40 alternatively or additionally relays the output of one or more camera 30, 130 to the cloud or other computer server 60, which includes the software and memory storage for analyzing and storing the output of one or more camera 30 for the user, e.g., for artificial intelligence purposes described herein.

As discussed above, the user's clinic, service or other interested entity computer 50 may include the software for analyzing the output of one or more camera 30, 130. The results of such analysis may be displayed or otherwise communicated at the computer 50 or be sent back to the user's smart device or smart phone 40 for display and/or other form of communication.

The user's clinic, service or other interested entity computer 50 may alternatively or additionally relay the output of one or more camera 30, 130 to cloud or other computer server 60, which includes the software and memory storage for analyzing and storing the output of one or more camera 30, 130 for the user, e.g., for artificial intelligence purposes described herein. The results of such analysis may be displayed or otherwise communicated, e.g., visually and/or audibly, at camera assembly 20 worn by the user, the user's smart device or smart phone 40, and/or at clinic, service, or other interested entity computer 50. Camera assembly 20, as discussed herein, may be provided with a display device, microprocessor, and video controller for analyzing and displaying the output of the analysis directly to the user, e.g., in real time or virtually in real time.

The relaying of any information described herein may performed wired or wirelessly. Also, either one or both of the application software at the user's smart device or smart phone 40 and the software used at interested entity computer 50 may be configured to modify, e.g., enlarge, brighten, trim, and/or quantify an aspect of the camera output from camera assembly before relaying the modified camera output to one or more computer server 60. Additionally, any of the camera outputs described herein may include one or more video images, a series of still images, and a combination of video and still images.

The inward looking one or more camera 30 is used in one embodiment to record the reaction to a stimulus given to or applied to the wearer of camera assembly 20. Example stimuli include prescription drugs, medicines or medicaments, homeopathic medicines, meditation, exercise, yoga, cannabis (including cannabidiol ("CBD") and other derivatives), a change in environment, and music.

The inward looking one or more camera 30 worn by the user may be focused, for analysis, on any one or more ocular or eye related feature or phenomenon, including the user's retina, visual cortex, eye movement (up/down, left/right), blinking, and eyebrow movement. The results of the analysis may be combined with the results from one or more other sensor, such as a blood pressure sensor, a pulse oximeter, a blood sugar sensor, and a user temperature sensor.

The analysis of the output of the one or camera may look to provide an indication of the mental state of the user, including but not limited to any one or more of the following: physical pain, stress, fear/anxiety, happiness/euphoria, calmness, concentration/focus, anger, and medical anomaly or disorder.

The analysis of the output of one or more camera 30, e.g., for any of the stimuli listed herein, and focusing on any ocular or eye related feature or phenomenon discussed herein, may compare the user's camera output results to a collective established outcome determiner, such as a baseline, threshold or range of results. Based on the comparison of the user's results to the outcome determiner, ocular feedback system 10 and its associated methodology of the present disclosure may form one or more conclusion, diagnosis, and/or recommendation. To establish the outcome determiner, e.g., baseline, threshold or range of results, it is contemplated to aggregate population data. Aggregating population data is one example where the many camera assemblies 20 are used by present system 10. Over time, as more data is collected from more and more different camera assemblies 20, and more results are verified, e.g., via outside testing, doctor's diagnosis, user input and collective agreement (e.g., 80 percent of people having particular camera result report feeling happiness/euphoria), the outcome determiner becomes better established and may be able to predict and provide more varied conclusions, diagnosis, and/or recommendations.

It is contemplated that the collective databases, e.g., stored at one or more interested entity computer 50 and/or one or more cloud or other server 60, be bolstered by additional user input. That is, the collective data is not just data from camera assemblies 20, but also data inputted by the user, which may help categorize, authenticate and corroborate camera output data. The user may for example provide data concerning other medications taken, known user health conditions, exercise habits, eating and drinking habits, for example, which are relevant to the particular analysis being performed. The user inputted data may be used to form sub-groups, e.g., for a Glaucoma analysis, the user's data may be compared to the whole population and/or to subgroups of users having the same conditions, such as age range, ethnicity, etc. Ocular feedback system 10 of the present disclosure becomes more confident in its conclusions and is able to make more and more varied conclusions as the data set, including camera assembly data and user input data, increases. Trending analysis may be possible based on a change in the conditions of users with certain ailments and treatments.

The analysis may be performed in real time and provide discrete tracking of the user, which facilitates comparison of the user's data to the outcome determiner developed from the population data, including any relevant subgroups. The outcome determiner may also be based on historical data for a particular user, e.g., wherein a trend based on the user's ocular results indicates that a certain user event is likely to happen. So the outcome determiner of the present disclosure does not have to be based on data from other (population) users and may alternatively or additionally be based on historical data for the particular user. Comparison of the user data with the population data may, for example, discover a user condition that is not the focus of the present analysis, e.g., based on data comparison similarities with subgroups of the population diagnosed with such conditions.

Goals of the collective population and individual data of ocular feedback system 10 is to provide a more accurate measure of the dosing of a medication, the effectiveness of treatment, and the selection of the best type of treatment.

Use Cases

The following set of use cases illustrate example ways and modes in which ocular feedback system 10 and its associated methodology of the present disclosure may be implemented both for the inward and outward looking one or more cameras 30, 130 of the present disclosure.

Workplace Efficiency Measurements

In the workplace efficiency use case, ocular feedback system 10 of the present disclosure is used to track the level of focus of an employees and to show when work is performed efficiently and when efficiency or quality has dropped. The user/worker wears camera assembly 20 at work. Camera assembly 20 here may output to a manager's computer 50 or to a server 60 located within the worksite facility, either or which may output to a company-wide server 60. Software at the manager's computer 50 or at one of servers 60 is configured, for example, to track the inward looking one or more camera 30 to detect if a user's eyes have wandered from a task. The software may track the outward looking camera to determine when a work throughput rate is high, medium or low. The outward looking camera may also be used to know when a worker has left their workstation or is oriented towards a non-working entity, e.g., is talking to another employee.

The results of the software analysis may be used for many purposes. For a given employee, the software may determine which shift of a workday is best for the user. The software may determine, e.g., on a pattern basis or a realtime basis, the best time for the worker to take a break. The software may determine if the employee works more efficiently at home or at the workplace. Ocular feedback system 10 may optimize the environment of the workspace of every employee by accessing for each employee different methods and schedules of working. The data collected by ocular feedback system 10 may be combined with other workplace data, e.g., workplace data developed internally or extrinsic workplace data, each of which may increase the accuracy of the system 10 data. Such a combination of system and internally developed or extrinsic data may be performed in any of the use cases discussed herein. The benefits of using present system 10 and its associated methodology at a workplace are many and include using the camera assembly data of an individualized workspace to heighten the level of efficiency and focus on the job.

Dosing

In the dosing use case, ocular feedback system 10 of the present disclosure generally involves the inward looking one or more camera 30 of the camera assemblies. For medical dosing, the user is provided a drug, medicine or medicament, e.g., orally, intravenously, topically, after which the output from one or more inward looking camera 30, recording a desired portion of the user's eye, is used as feedback to judge the effect of the drug. Use of ocular feedback system 10 for medical dosing allows for more specific and granular control, which is based on individual need and circumstances instead of set standard based on certain qualifications (age, weight, etc.). Use of the present ocular feedback system 10 for medical dosing aids in preventing the user from receiving an inadequate or excessive dose because, in an embodiment, rather than receiving a fixed dose, dosing is monitored using feedback until the output from one or more camera 30 of camera assembly 20 indicates an appropriate response from the user's eye. The output of camera 30 may show a change in the user's condition in real time due to the medication received.

Use of ocular feedback system 10 for medical dosing also allows for an optimal dose timing interval to be determined, which may, for example, take into account at least one of a drug's half-life, the user's delayed reaction to the drug, or other factors particular to the drug, the user, or the user's condition. In an example, instead of an anxiety patient/user being given a standard time interval between doses of the anxiety medication, ocular feedback system 10 uses the user's eye response output from camera assembly 20 to determine what frequency of dosing is most effective for the particular user.

Use of ocular feedback system 10 for recreational dosing allows for the effects of the consumption of a recreational drug (e.g., marijuana, alcohol) to be measured based on the output of the camera assembly's one or more inward looking camera focused on a destined portion of the user's eye, e.g., retina. Ocular feedback system 10 may allow the user to consume an optimal amount of the recreational drug, may inform the user of the threshold of effectiveness of the drug or the threshold to damaging impacts of the drug to avoid overuse and/or to avoid driving or operating equipment after a certain threshold. Ocular feedback system 10 of the present disclosure may also be linked to a telephone service 80 (FIG. 1 shown interacting with computer 50 and/or server 60, but could be linked to smart device 40 also) that places an automatic call to an emergency number if the software based on the output of inward looking camera 30 determines that too much of the recreational drug has been taken.

Use of ocular feedback system 10 for therapeutic dosing allows for the effects of therapeutic activities, e.g., psychotherapy, meditation, breathing exercises, yoga, and the like, to be monitored and optimized. The inward looking one or more camera 30 monitors the user's eye, e.g., retinal response to a therapeutic activity to determine if it has an effect on the user. Ocular feedback system 10 may employ population data and artificial intelligence for a comparison to the user's ocular response to different therapeutic activities to determine which one or more is best for the user (e.g., yoga versus breathing exercises).

Medical Diagnosis

In the medical diagnosis use case, ocular feedback system 10 of the present disclosure generally involves the inward looking one or more camera 30 of the camera assemblies 20 in combination with the use of population data and artificial intelligence via storage at one or more centralized computer server 60. Feedback from many camera assemblies 20 associated with many different users in combination with additional input from the users concerning their particular ailment is used to build a population database for each ailment, e.g. stored at system computer 50 or server 60.

Ocular feedback system 10 then compares the output from one or more inward-looking camera 30 of camera assembly 20 worn by the user to the established ailment database results to determine if the user may have or be inclined to have a particular ailment.

The population data, or a subgroup of it, also allows ocular feedback system 10 to determine one or more normal (user without an ailment) characteristic for eye, e.g., retinal, behavior. Here, ocular feedback system 10 may compare the output from one or inward-looking camera 30 of camera assembly 20 worn by the user to see if their exhibited ocular behavior is within the statistical norm of the population, or a specific subset.

Ocular feedback system 10 may also look to a user's past or historical data to make a diagnostics. Here, system computer 50 or server 60 stores the user's eye or retinal behavior for a time in which the user is known to have a particular ailment. If the user's present ocular output matches or begins to match the known ailment output, system 10 may notify the user, e.g., via the user's smart device 40, to check to see if the ailment has returned. Historical user data may also include treatment data for the ailment, e.g., ocular data collected at the start, middle, and end of treatment, to show the historical effects of treatment. Ocular feedback system 10 may then compare the historical treatment data for a particular ailment to the user's current ocular data to show positive, negative or lack of impact on the user's condition.

Effectiveness of Treatment

In the effectiveness of treatment use case, ocular feedback system 10 of the present disclosure generally involves the inward looking one or more camera 30 of the camera assemblies 20 in combination with the use of population data and artificial intelligence via storage at one or more system computer 50 or centralized computer server 60. Effectiveness of treatment also requires input from the users regarding how they are feeling and if the symptoms of the ailment for which they have been treated still persist or have gone away. Population data is used to determine an expected impact (or range of impacts) for a particular treatment.

In an embodiment, ocular feedback system 10 is used to evaluate the user initially to determine a baseline and a treatment plan for the user. System 10 may then evaluate the effectiveness of the treatment plan on a short term basis and a long term basis. In the short term, the results from the inward looking one or more camera 30 of the user's camera assembly 20 are compared to an expected one or more impact determined via population data. In the short term, the software of system 10 builds a historical trend for the user in an effort to determine if the treatment is effective or not based on declining (or not) symptoms of the user's particular ailment, wherein the declining of the symptoms may be measured based on a decrease in length, intensity, or other marker of change for the symptom. In the example ailment of post-traumatic stress disorder ("PTSD"), the user's ingestion of cannabidiol ("CBD") has been shown to have beneficial effects. Ocular feedback system 10 records the user's administration of CBD and the output from inward looking camera 30 recording the user's the eye. That information is then cross-referenced by system 10 using information from the user concerning whether the user's PTSD symptoms have or have not gotten shorter, less frequent, less severe, etc. In the short term, the PTSD users may show a desirable outcome of the treatment. In the long term PTSD users may show a decline in frequency, intensity, length, etc., of a PTSD episode or symptom.

Real World Environment Effects on Mental State

In the real world environment effects on mental state of treatment use case, ocular feedback system 10 of the present disclosure involves the inward looking one or more camera 30 and the outward looking one or more camera 130 of the camera assemblies 20 in combination with the use of population data and artificial intelligence via storage at one or more system computer 50 or centralized computer server 60. In an embodiment, ocular feedback system 10 uses the outward looking one or more camera 130 to record and digitize the external environment that the user is seeing. At the same time, ocular feedback system 10 uses the inward looking one or more camera 30 to evaluate the user's ocular, e.g., retinal response. System 10 uses population data and artificial intelligence to establish baselines and categories used to evaluate the user's ocular response. Here, artificial intelligence and data analysis via the software of ocular system 10 forms correlations between emotional states (inward looking camera results) and environmental factors (outward looking camera results). The correlations may for example include an outward looking camera output cause and an inward looking camera output effect.

It is further contemplated that ocular feedback system 10 builds a historical database for the user, stored at system computer 50 or centralized computer server 60, which may be used predict reactions for new encounters based on recorded correlations for the user in past encounters. In an example, population data is used to determine from inward looking camera results a peacefulness level for the user. System 10 then uses the outward looking camera results to correlate that the user is more peaceful in botanical setting than a beach setting. Ocular feedback system 10 here also includes a user interface that is able to provide the user with ideas, e.g., where to go to relax, where to go to have excitement, etc. The user interface may, for example, be a software application for ocular feedback system 10 that is downloaded onto the user's smart device or smart phone 40.

Visual and Audio Impacts on Mental and Physiological State

In the real world environment effects on mental state of treatment use case, ocular feedback system 10 of the present disclosure involves the outward looking one or more camera 130 of camera assemblies 20 in combination with the use of population data and artificial intelligence via storage at one or more system computer 50 or centralized computer server 60. Here, after collecting significant levels of user data, the user interface of ocular feedback system 10 is able to suggest solutions that are pharmaceutical or other in nature. In an example, the user communicates via the user interface that the user is experiencing stress. Ocular feedback system 10 responds at the user interface, e.g., smart device 40, to listen to calming nature sounds based on historical data of successful stress decline that had occurred and been recorded by system 10 in the past. System 10 here does not require new data from inward looking camera 30 (except perhaps as confirmation on the effectiveness of the system suggestion). System 10 here instead is answering a query from the user. Historical data is used to identify the best one or more solution to the user's ailment and associated inquiry. The more data that ocular feedback system 10 is able to collect, the more accurate a solution (and range of solutions) that present system 10 is able prescribe to the individual user.

Determine and Implement Best Realtime Treatment Using Artificial Intelligence In the determine and implement best realtime treatment use case, ocular feedback system 10 of the present disclosure involves the inward and outward looking one or more camera 30, 130 of camera assemblies 20 in combination with the use of population data and artificial intelligence via storage at one or more centralized computer server 60. Population data and artificial intelligence are used to select the best realtime treatment for the user regarding any one or more of: (i) determining proper or most effective dosing levels, (ii) determining the most effective treatment plan for the user based on existing conditions and environment, (iii) determining the effectiveness of a user's treatment plans over time (historical trends), (iv) determining if the user is experiencing conditions outside of normal conditions, e.g., using historical data analysis and trending, the artificial intelligence software of ocular feedback system 10 of the present disclosure is able to extrapolate potential or existing issues for the user.

Continuous and Periodic Usage

The continuous versus periodic usage use case involves how long the user wears or dons camera assembly 20 of ocular feedback system 10 of the present disclosure. Situations in which the outward looking one or more camera 130 of camera assemblies 20 is/are used (e.g., in combination with inward looking cameras 30) tend to require longer and more continuous usage. Examples include the workplace efficiency and environmental effects use cases discussed above. In the workplace efficiency example, a continuous data stream is analyzed by the system software at system computer 50 or centralized server 60 to place the video output into one or more different bucket or category, e.g., efficient or workplace engaged versus non-efficient or workplace disengaged. In the environmental effects use case, continuous use is needed because it is not known when a correlating event between what the user sees (recorded by one or more outward looking camera 130) and how the user reacts (recorded by one or more inward looking camera 30) is going to occur.

Periodic usage generally involves the use of the inward looking one or more camera 30 of the camera assemblies 20. For many situations, the user here does not need to continuously wear camera assembly 20. For example, the ocular examination, e.g., of the user's retina, may only require a duration needed to determine the effect of a drug or medicament consumed. System software at system computer 50 or centralized server 60, e.g., in assessing dosing, looks to the output of one or more inward looking camera 30 over a time needed to determine that the user is properly dosed. Even determining long term effectiveness of a treatment in an embodiment may only require the summation of short, periodic camera assembly 20 usage and data collection.

It should be understood that other changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An ocular feedback system comprising:
   a first camera assembly including a first frame worn by a first user and at least one first camera supported by the first frame, the at least one first camera positioned and arranged to produce a first camera output concerning at least one eye of the first user;
   a second camera assembly including a second frame worn by a second user and at least one second camera supported by the second frame, the at least one second camera positioned and arranged to produce a second camera output concerning at least one eye of the second user; and
   at least one computer configured to build an established outcome determiner based on an analysis of the first camera output and the second camera output, the at least one computer configured to compare the established outcome determiner to at least one third camera output concerning at least one eye of a third user taken by at least one third camera supported by a third frame of a third camera assembly worn by the third user.

2. The ocular feedback system of claim 1, wherein the at least one computer is further configured to form one or more conclusion from the comparison of the established outcome determiner to the at least one third camera output.

3. The ocular feedback system of claim 2, wherein the one or more conclusion includes a dose determination for a drug taken by the third user prior to or while wearing the third camera assembly.

4. The ocular feedback system of claim 2, wherein the one or more conclusion includes an effectiveness determination for a drug taken by the third user prior to or while wearing the third camera assembly.

5. The ocular feedback system of claim 1, wherein the at least one computer is further configured to form a diagnosis from the comparison of the established outcome determiner to the at least one third camera output.

6. The ocular feedback system of claim 1, wherein the at least one computer is further configured to form a recommendation from the comparison of the established outcome determiner to the at least one third camera output.

7. The ocular feedback system of claim 1, wherein the established outcome determiner includes a range of results from the analysis of the first camera output and the second camera output.

8. The ocular feedback system of claim 1, wherein the established outcome determiner includes a threshold or baseline result from the analysis of the first camera output and the second camera output.

9. The ocular feedback system of claim 1, wherein the established outcome determiner is further built based on input to the at least one computer from at least one of the first or second users.

10. The ocular feedback system of claim 1, wherein the established outcome determiner is further built based on input to the at least one computer from at least one third party, optionally a medical professional.

11. The ocular feedback system of claim 1, wherein the established outcome determiner is subsequently further built based on analysis of the at least one third camera output.

12. The ocular feedback system of claim 1, wherein the first, second, and third camera outputs attempt to record a change in a retina of at least one of the first, second, and third user's eyes.

13. The ocular feedback system of claim 1, wherein the at least one computer is a computer server placed in communication with at least one smart device configured to relay at least one of the first, second, and third camera outputs to the computer server.

14. The ocular feedback system of claim 13, wherein the at least one smart device is provided with a software application configured to receive one of the first, second, or third camera outputs.

15. The ocular feedback system of claim 14, wherein the software application is configured to modify the first, second, or third camera output from the first, second, or third at least one camera, respectively, prior to relaying the modified first, second, or third camera output to the computer server.

16. The ocular feedback system of claim 1, wherein the at least one computer is a computer server placed in communication with at least one interested entity computer configured to relay at least one of the first, second, and third camera outputs to the computer server.

17. The ocular feedback system of claim 16, wherein the at least one interested entity computer is provided with software configured to receive one of the first, second, or third camera outputs.

18. The ocular feedback system of claim 17, wherein the at least one interested entity computer is configured to modify the first, second, or third camera output from the first, second, or third at least one camera, respectively, prior to relaying the modified first, second, or third camera output to the computer server.

19. The ocular feedback system of claim 1, wherein the first, second, or third camera outputs include one or more video images, a series of still images, and a combination of video and still images.

20. An ocular feedback system comprising:

a frame wearable by a user;

at least one inward looking camera supported by the frame, the at least one inward looking camera positioned and arranged to produce an inward looking camera output concerning at least one of eye the user;

at least one outward looking camera supported by the frame, the at least one outward looking camera positioned and arranged to produce an outward looking camera output concerning an environment of the user; and at least one computer configured to form a correlation between the inward looking camera output and the outward looking camera output, wherein the correlation between the inward looking camera output and the outward looking camera output includes a cause based on the outward looking camera output and an effect determined from the inward looking camera output.

21. An ocular feedback system comprising:

a frame wearable by a user;

at least one camera supported by the frame, the at least one camera positioned and arranged to take at least one image of at least one eye of the user;

at least one computer configured to analyze the at least one image so as to focus the at least one image on at least one pupil of the at least one eye of the user, the at least one computer further configured to (i) determine a quantification of an amount of dilation of the at least one pupil, and (ii) determine an outcome for the user based on the quantification; and at least one memory configured to store historical data for the user, the historical data used by the at least one computer in determining the outcome for the user.

22. The ocular feedback system of claim 21, wherein the at least one camera is a video camera, and wherein the at least one image is a video image.

23. The ocular feedback system of claim 21, wherein the frame is configured to be supported by a nose and ears of the user.

24. The ocular feedback system of claim 21, wherein the frame is attached to a strap configured to be worn about a user's head.

25. The ocular feedback system of claim 21, wherein the frame includes at least one extension, the at least one camera attached to the at least one extension, the at least one extension configured to move the at least one camera away from the at least one eye of the user.

26. The ocular feedback system of claim 21, further comprising at least one lens supported by the frame, and wherein at least one of the at least one camera is attached to the at least one lens.

27. The ocular feedback system of claim 21, wherein the at least one computer is supported by the frame or is a separate at least one computer.

28. The ocular feedback system of claim 27, which includes a power supply configured to power the at least one camera, the power supply supported by the frame, wherein the power supply is rechargeable.

29. The ocular feedback system of claim 21, wherein the at least one memory is supported by the frame or is a separate memory.

30. The ocular feedback system of claim 21, wherein the at least one computer is configured to communicate with a remote device, the remote device configured to at least one of determine or display the outcome.

31. The ocular feedback system of claim 21, wherein the outcome is indicative of an effectiveness of a drug.

32. The ocular feedback system of claim 21, wherein the at least one camera is an inward looking camera, and which includes at least one outward looking camera supported by the frame.

33. The ocular feedback system of claim 32, wherein the at least one computer is further configured to correlate at least one video image from the at least one outward looking camera with the at least one video image from the inward looking camera so as to focus the at least one image on at least one pupil of the at least one eye of the user, the at least one computer further configured to (i) determine a quantification of an amount of dilation of the at least one pupil, and (ii) determine an outcome for the user based on the quantification.

* * * * *